(12) United States Patent
Becker et al.

(10) Patent No.: US 9,073,840 B2
(45) Date of Patent: *Jul. 7, 2015

(54) OXIDATION OF HYDROCARBONS

(75) Inventors: Christopher L. Becker, Manhattan, KS (US); Jihad M. Dakka, Whitehouse Station, NJ (US); Francisco M. Benitez, Cypress, TX (US); Edmund J. Mozeleski, Califon, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 27 days.

This patent is subject to a terminal disclaimer.

(21) Appl. No.: 13/816,125

(22) PCT Filed: Aug. 16, 2011

(86) PCT No.: PCT/US2011/047852
§ 371 (c)(1),
(2), (4) Date: Apr. 26, 2013

(87) PCT Pub. No.: WO2012/036829
PCT Pub. Date: Mar. 22, 2012

(65) Prior Publication Data
US 2013/0203984 A1     Aug. 8, 2013

Related U.S. Application Data

(60) Provisional application No. 61/503,071, filed on Jun. 30, 2011, provisional application No. 61/382,776, filed on Sep. 14, 2010.

(51) Int. Cl.
| | | |
|---|---|---|
| C07C 409/08 | (2006.01) | |
| C07C 407/00 | (2006.01) | |
| C07C 2/74 | (2006.01) | |
| C07C 29/50 | (2006.01) | |
| C07C 37/08 | (2006.01) | |
| C07C 45/33 | (2006.01) | |
| C07C 45/53 | (2006.01) | |
| C07C 51/31 | (2006.01) | |
| C07C 29/48 | (2006.01) | |
| C07C 45/28 | (2006.01) | |
| C07C 51/00 | (2006.01) | |
| C07C 51/16 | (2006.01) | |
| C07C 51/21 | (2006.01) | |
| C07D 223/10 | (2006.01) | |

(52) U.S. Cl.
CPC ............ *C07C 407/00* (2013.01); *C07C 409/08* (2013.01); *C07C 2/74* (2013.01); *C07C 29/50* (2013.01); *C07C 37/08* (2013.01); *C07C 45/33* (2013.01); *C07C 45/53* (2013.01); *C07C 51/316* (2013.01); *C07C 2101/14* (2013.01); *C07C 29/48* (2013.01); *C07C 45/28* (2013.01); *C07C 51/00* (2013.01); *C07C 51/16* (2013.01); *C07C 51/21* (2013.01); *C07D 223/10* (2013.01)

(58) Field of Classification Search
CPC ....................................................... C07C 409/08
USPC .......................................................... 568/569
See application file for complete search history.

(56) References Cited

U.S. PATENT DOCUMENTS

| | | | |
|---|---|---|---|
| 6,720,462 | B2 | 4/2004 | Kuhnle et al. |
| 6,852,893 | B2 | 2/2005 | Kuhnle et al. |
| 7,038,089 | B2 | 5/2006 | De Frutos Escrig et al. |

FOREIGN PATENT DOCUMENTS

| | | |
|---|---|---|
| EP | 0 463 535 | 1/1992 |
| EP | 2 098 505 | 9/2009 |
| WO | 2009/058531 | 5/2009 |
| WO | 2010/042273 | 4/2010 |

OTHER PUBLICATIONS

Schuchardt et al., "*Cyclohexane Oxidation Continues to be a Challenge*", Applied Catalysis A: General, 2001, vol. 211, pp. 1-17.

*Primary Examiner* — Robert Havlin
(74) *Attorney, Agent, or Firm* — Siwen Chen; Stephen A. Baehl

(57) ABSTRACT

In a process for oxidizing a hydrocarbon to a product comprising at least one of the corresponding hydroperoxide, alcohol, ketone, carboxylic acid and dicarboxylic acid, the hydrocarbon is contacted with an oxygen-containing compound in at least one oxidation zone in the presence of a catalyst comprising a cyclic imide having an imide group of formula (I):

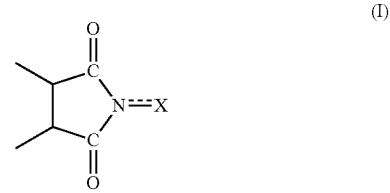

(I)

wherein X represents an oxygen atom, a hydroxyl group, or an acyloxy group and wherein the oxygen-containing compound supplied to said at least one oxidation zone has a water content of less than or equal to 0.6% by weight of the oxygen-containing compound.

16 Claims, 1 Drawing Sheet

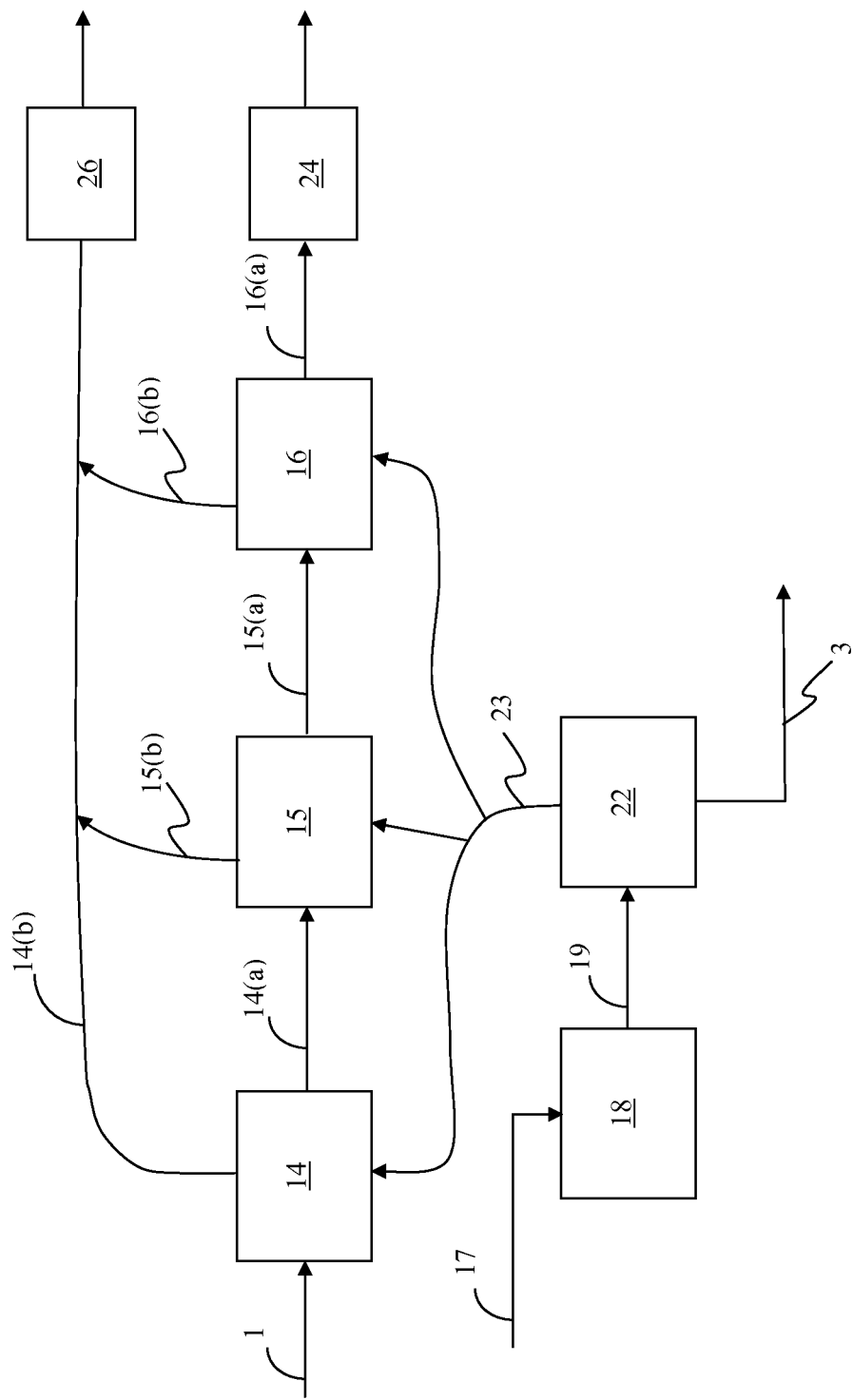

OXIDATION OF HYDROCARBONS

PRIORITY CLAIM

This application is a National Stage Application of International Application No. PCT/US2011/047852 filed Aug. 16, 2011, which claims priority to and the benefit of U.S. Provisional Application Ser. No. 61/503,071 filed Jun. 30, 2011 and 61/382,776 filed Sep. 14, 2010 the disclosures of which are fully incorporated herein by their reference in their entirety.

FIELD

The present invention relates to a process for oxidizing hydrocarbons and, in particular, alkylaromatic hydrocarbons.

BACKGROUND

The oxidation of hydrocarbons is an important reaction in industrial organic chemistry. Thus, for example, the oxidation of cyclohexane is used commercially to produce cyclohexanol and cyclohexanone, which are important precursors in the production of nylon, whereas oxidation of alkylaromatic hydrocarbons is used in the production of phenol, a precursor in the manufacture of polycarbonates and epoxy resins.

Oxidation of hydrocarbons can be conducted using well-known oxidizing agents, such as $KMnO_4$, $CrO_3$, and $HNO_3$. However, these oxidizing agents have the disadvantage of being relatively expensive, and moreover their use is accompanied by the production of unwanted coupling products which can represent disposal problems and ecological pollution.

Preferably, therefore, oxidizing agents based on peroxides or $N_2O$ are used. The cheapest oxidizing agent, however, is molecular oxygen, either in pure form or as atmospheric oxygen. However, oxygen itself is usually unsuitable for oxidizing hydrocarbons, since the reactivity of the $O_2$ molecule, which occurs in the energetically favorable triplet form, is not sufficient.

By using redox metal catalysts it is possible to utilize molecular oxygen for oxidizing organic compounds and hence a great number of industrial processes are based on the metal-catalyzed autooxidation of hydrocarbons. Thus, for example, the oxidation cyclohexane with $O_2$ to cyclohexanol and/or cyclohexanone proceeds with the use of cobalt salts. These industrial processes are based on a free-radical chain mechanism, in which the bi-radical oxygen reacts with a hydrocarbon free radical, with formation of a peroxy radical and subsequent chain propagation by abstraction of an H atom at a further hydrocarbon. In addition to metal salts, however, organic molecules can also act as free-radical initiators.

However, it is a disadvantage of these processes that the selectivity decreases very greatly with increasing conversion rate and therefore the processes must be operated at a very low level of conversion rate. Thus, for example, the oxidation of cyclohexane to cyclohexanol/cyclohexanone is carried out at a conversion rate of 4 to 7% so that the selectivity is 80 to 85% (Ulf Schuchardt, et. al., *Applied Catalysis A: General*, 211 (2001) 8).

An alternative to metal salt catalysts is the use of organic mediators, for example N-hydroxyphthalimide (NHPI). Thus, U.S. Pat. Nos. 6,852,893 and 6,720,462 describe methods for oxidizing hydrocarbon substrates by contacting the substrate with an oxygen-containing gas, in which the oxygen content is from 5 to 100% by volume, in the presence of a free radical initiator and a catalyst, typically an N-hydroxycarbodiimide catalyst, such as N-hydroxyphthalimide (NHPI). The process is conducted at a temperature between 0° C. and 500° C. and a pressure between atmospheric and 100 bar (100 and 10,000 kPaa). The molar ratio of the catalyst to the hydrocarbon substrate can range from $10^{-6}$ mol % to 1 mol %, whereas the molar ratio of free-radical initiator to the catalyst can be 4:1 or less, such as 1:1 to 0.5:1. Suitable substrates that may be oxidized by this process include cumene, cyclohexylbenzene, cyclododecylbenzene, and sec-butylbenzene.

U.S. Pat. No. 7,038,089 discloses a process for preparing a hydroperoxide from a hydrocarbon selected from a group consisting of primary hydrocarbons, secondary hydrocarbons and mixtures thereof corresponding to said hydroperoxide which comprises conducting oxidation of said hydrocarbon at a temperature in the range between 130° C. and 160° C. with an oxygen-containing gas in a reaction mixture containing said hydrocarbon and a catalyst comprising a cyclic imide compound and an alkali metal compound. Suitable hydrocarbons are said to include $C_4$ to $C_{20}$ tertiary alkanes (e.g., iso-butane, iso-pentane, iso-hexane, and the like), $C_7$ to $C_{20}$ (alkyl) aromatic hydrocarbons with 1 to 6 aromatic rings or $C_9$ to $C_{20}$ (cycloalkyl) aromatic hydrocarbons with 1 to 6 aromatic rings (e.g., xylene, cumene, cymene, ethylbenzene, diisopropylbenzene, cyclohexylbenzene, tetrahydronaphthalene (tetraline), indane, etc.), and the like. The amount of the cyclic imide compound used may be from 0.0001 to 1%, preferably from 0.0005 to 0.5%, by weight based on the reaction mixture, whereas the amount of the alkali metal compound may be from 0.000005 to 0.01%, preferably from 0.00001 to 0.005%, by weight based on the reaction mixture.

However, although current work has continued to demonstrate the utility of cyclic imides as hydrocarbon oxidation catalysts, it has also shown that their application in a commercial process requires further investigation. In particular, cyclic imides, such as N-hydroxyphthalimide, are expensive and are readily hydrolyzed under the conditions of the oxidation reaction. Since water is inherently generated in the oxidation process, loss of catalyst through hydrolysis represents a significant problem to the commercial viability of the process.

According to the invention, it has now been found that, despite the inherent generation of water in the process, the problem of catalyst loss through hydrolysis during the oxidation of hydrocarbons using cyclic imide catalysts can be significantly reduced by at least partially drying the oxygen-containing gas used in the oxidation to a water level of 0.6% by weight or less. This can be readily achieved by the simple expedient of compressing and/or cooling the oxygen-containing gas to a temperature of about 3° C. to about 20° C. and then passing the gas through a gas/liquid separator. If desired, lower levels of water can be achieved by passing the oxygen-containing gas through a molecular sieve.

SUMMARY

In one aspect, the invention resides in a process for oxidizing a hydrocarbon to a product comprising at least one of the corresponding hydroperoxide, alcohol, ketone, carboxylic acid and dicarboxylic acid, the process comprising contacting a hydrocarbon with an oxygen-containing compound, such as air, in at least one oxidation zone in the presence of a catalyst comprising a cyclic imide having an imide group of formula (I):

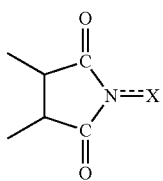

(I)

wherein X represents an oxygen atom, a hydroxyl group, or an acyloxy group and wherein the oxygen-containing compound supplied to said at least one oxidation zone has a water content of less than or equal to 0.6% by weight, such as less than or equal to 0.3% by weight of the oxygen-containing compound.

In one embodiment, the hydrocarbon comprises an alkane or cycloalkane, such as isobutane or cyclohexane.

In another embodiment, the hydrocarbon comprises an alkylaromatic compound of general formula (II):

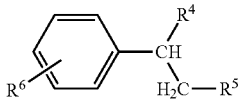

(II)

wherein $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group and the product comprises a hydroperoxide of the general formula (III):

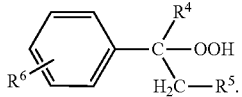

(III)

Conveniently, said alkylaromatic compound of general formula (II) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

Conveniently, the process further comprises cleaving the hydroperoxide to produce phenol or a substituted phenol.

In one embodiment, said cyclic imide is of the general formula (IV):

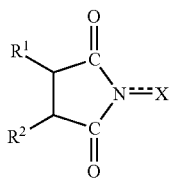

(IV)

wherein X represents an oxygen atom, a hydroxyl group, or an acyloxy group and $R^1$ and $R^2$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^1$ and $R^2$ may be bonded together to form a double bond or an aromatic- or non-aromatic ring.

In another embodiment, said cyclic imide is of the general formula (V):

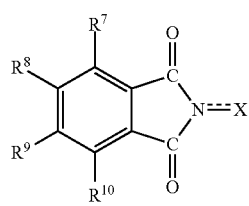

(V)

wherein X represents an oxygen atom, a hydroxyl group and each of $R^7$, $R^8$, $R^9$, and $R^{10}$ is independently selected from H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I and/or $NO_2$.

Conveniently, said cyclic imide comprises N-hydroxyphthalimide.

In one embodiment, the process further comprises:

(a) cooling an oxygen-containing gas stream to a temperature of less than about 20° C. between, such as about 3° C. and about 20° C., such as between about 5° C. and about 10° C., and/or pressurizing said gas stream to a pressure between about 50 kPa, gauge to about 1000 KPa, gauge, such as between about 150 kPa, gauge to about 500 KPa, gauge;

(b) passing the cooled and/or pressurized gas stream through a gas/liquid separator to reduce the water content of said gas stream to less than or equal to 0.6% by weight; and (c) supplying said gas stream from (b) to said at least one oxidation zone as the oxygen-containing compound.

In further embodiment, the process comprises:

(d) passing an oxygen-containing gas stream through a bed of a molecular sieve, such as zeolite 4A, which is effective to remove water from said stream and produce a dried gas stream containing less than or equal to 0.1% by weight of water; and (e) supplying said dried gas stream said at least one oxidation zone.

In further embodiment, the process comprises:

(a) cooling an oxygen-containing gas stream to a temperature of less than about 20° C., such as between about 5° C. and about 10° C., and/or pressurizing said gas stream to a pressure between about 50 KPa, gauge to about KPa, gauge, such as between about 150 KPa, gauge to about 500 KPa, gauge;

(b) passing the cooled and/or pressurized gas stream through a gas/liquid separator to reduce the water content of said gas stream to less than or equal to 0.6% by weight;

(c) passing the gas stream from (b) through a bed of a molecular sieve, such as zeolite 4A, which is effective to remove further water from said stream and produce a dried gas stream containing less than or equal to 0.1% by weight of water; and (d) supplying said dried gas stream to said at least one oxidation zone as the oxygen-containing compound.

In further embodiment, the process comprises:

(a) hydroalkylating benzene with hydrogen in the presence of a hydroalkylation catalyst under conditions effective to produce a hydroalkylation reaction product comprising cyclohexylbenzene;

(b) separating at least a portion of the cyclohexylbenzene from the hydroalkylation reaction product;

(c) obtaining dehydrated air having a water content of less than or equal to 0.6% by weight;

(d) contacting at least a portion of the cyclohexylbenzene from the separating step (b) with the dehydrated air in the presence of an oxidation catalyst comprising a cyclic imide in an oxidation zone under oxidation conditions effective to produce an oxidation product comprising cyclohexylbenzene hydroperoxide and cyclic imide catalyst; and (e) contacting at least a portion of the oxidation product comprising cyclohexylbenzene hydroperoxide with a cleavage catalyst under cleavage conditions effective to convert at least part of the cyclohexylbenzene hydroperoxide into phenol and cyclohexanone.

BRIEF DESCRIPTION OF THE DRAWINGS

FIG. 1 is a simplified flow diagram of a process for oxidizing a hydrocarbon according to one example of the present invention.

DETAILED DESCRIPTION OF THE EMBODIMENTS

Described herein is a process for oxidizing a hydrocarbon to a product comprising at least one of the corresponding hydroperoxide, alcohol, ketone, carboxylic acid, and dicarboxylic acid. In the present process, a feedstream comprising the desired hydrocarbon is contacted with an oxygen-containing compound, (e.g., gas), such as air (e.g., ambient air), in at least one oxidation zone in the presence of a catalyst comprising a cyclic imide. Despite the fact that cyclic imide catalysts are generally hydrolyzable in the presence of water and the oxidation process inherently generates water, it is found that the loss of catalyst during the oxidation process can be significantly reduced if the water content of the oxygen-containing compound supplied to the oxidation zone is reduced to less than or equal to 0.6% by weight of the compound, such as less than or equal to 0.5% by weight of the compound, such as less than or equal to 0.4% by weight of the compound, such as less than or equal to 0.3% by weight of the compound, such as less than or equal to 0.2% by weight of the compound, even less than or equal to 0.1% by weight of the compound.

Hydrocarbon Feed

Using the present process a wide group of substituted or unsubstituted saturated or unsaturated hydrocarbons, such as alkanes, cycloalkanes, alkenes, cycloalkenes, and aromatics, can be selectively oxidized. In particular, however, the process has utility in the selective oxidation of isobutane to tertiary butyl hydroperoxide and tertiary butanol, the selective oxidation of cyclohexane to cyclohexyl hydroperoxide, cyclohexanol and cyclohexanone and the selective oxidation to the corresponding hydroperoxides of alkylaromatic compounds of the general formula (II):

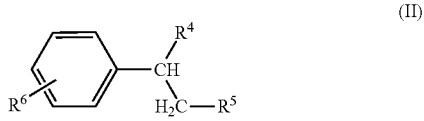

(II)

in which $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group. In one embodiment, $R^4$ and $R^5$ are joined to form a cyclic group having from 4 to 10 carbon atoms, conveniently a cyclohexyl group, substituted with one or more alkyl group having from 1 to 4 carbon atoms or with one or more phenyl groups. Examples of suitable alkylaromatic compounds are ethyl benzene, cumene, sec-butylbenzene, sec-pentylbenzene, p-methyl-sec-butylbenzene, 1,4-diphenylcyclohexane, sec-hexylbenzene, and cyclohexylbenzene, with sec-butylbenzene and cyclohexylbenzene being preferred. It will also be understood that in the case where $R^1$ and $R^2$ are joined to form a cyclic group, the number of carbons forming the cyclic ring is from 4 to 10. However, that ring may itself carry one or more substituents, such as one or more alkyl groups having from 1 to 4 carbon atoms or one or more phenyl groups, as in the case of 1,4-diphenylcyclohexane.

In one practical embodiment, the alkylaromatic compound of general formula (II) is sec-butylbenzene and is produced by alkylating benzene with at least one $C_4$ alkylating agent under alkylation conditions and in the presence of a heterogeneous catalyst, such as zeolite Beta or more preferably at least one molecular sieve of the MCM-22 family (as defined below). The alkylation conditions conveniently include a temperature of from about 60° C. to about 260° C., for example between about 100° C. and about 200° C. The alkylation pressure is conveniently 7000 kPa or less, for example from about 1000 to about 3500 kPa. The alkylation is conveniently carried out at a weight hourly space velocity (WHSV) based on $C_4$ alkylating agent of between about 0.1 and about 50 $hr^{-1}$, for example between about 1 and about 10 $hr^{-1}$.

The $C_4$ alkylating agent conveniently comprises at least one linear butene, namely butene-1, butene-2, or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in any refinery employing steam cracking to produce olefins and are suitable for use as the $C_4$ alkylating agent: a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream).

In a further practical embodiment, the alkylaromatic compound of general formula (II) is cyclohexylbenzene and is produced by contacting benzene with hydrogen in the presence of a heterogeneous bifunctional catalyst which comprises at least one metal having hydrogenation activity, typically selected from the group consisting of palladium, ruthenium, nickel and cobalt, and a crystalline inorganic oxide material having alkylation activity, typically at least one molecular sieve of the MCM-22 family (as defined below). The contacting step is conveniently conducted at a temperature of about 50° C. to about 350° C. The contacting pressure may be, for example, from about 100 to about 7000 kPa. The benzene to hydrogen molar ratio in the contacting step is preferably from about 0.01 to about 100. The WHSV during the contacting step is preferably in the range of about 0.01 to about 100.

The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

Hydrocarbon Oxidation

The oxidation step in the present process is accomplished by contacting the hydrocarbon substrate with an oxygen-containing compound (e.g., air) in the presence of a catalyst comprising a cyclic imide having an imide group of formula (I):

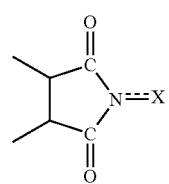

wherein X represents an oxygen atom, a hydroxyl group, or an acyloxy group.

Generally, the cyclic imide employed as the oxidation catalyst is of the general formula IV:

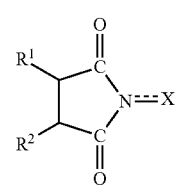

wherein X represents an oxygen atom, a hydroxyl group, or an acyloxy group and $R^1$ and $R^2$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^1$ and $R^2$ may be bonded together to form a double bond or an aromatic- or non-aromatic ring.

More specifically, the cyclic imide employed as the oxidation catalyst typically is of the general formula V:

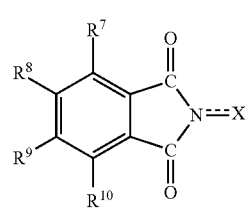

wherein X represents an oxygen atom, a hydroxyl group and each of $R^7$, $R^8$, $R^9$, and $R^{10}$ is independently selected from H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I, and/or $NO_2$.

In one practical embodiment, the cyclic imide catalyst comprises N-hydroxyphthalimide.

The oxidizing agent employed in the present oxidation process is an oxygen-containing gas, generally air, which has been dried to reduce its water content to less than or equal to 0.6% by weight, such as less than or equal to 0.3% by weight, even less than or equal to 0.1% by weight. Depending on the extent of water reduction desired, drying can be effected by cooling and/or pressurization of the gas or by passing the gas through a molecular sieve drier or a combination of these two methods.

In most cases, where drying to water levels greater than 0.1 wt % is sufficient, drying is conveniently achieved by cooling the oxygen-containing gas stream to a temperature of less than 20° C., such as between about 3° C. and about 20° C., such as between about 5° C. and about 10° C., and/or pressurizing said gas stream to a pressure between about 50 KPa, gauge to about 1000 KPa, gauge, such as between about 150 KPa, gauge to about 500 KPa, gauge. The cooling and/or pressurization causes part of the water vapor in the gas stream to condense and so the gas stream is then passed through a gas/liquid separator to remove the liquid water and reduce the water content of the gas stream to less than or equal to 0.6% by weight. The dried gas stream can then be fed to the oxidation reaction.

To illustrate the effect of cooling and pressurization on the water vapor content of an oxygen-containing gas stream, Table 1 gives the weight fraction of water vapor in air at a pressure of 1.5 barg, 150 KPa, gauge and various temperatures between 3° C. and 20° C.

TABLE 1

| Temperature (° C.) | Wt fraction water in air (wt %) |
|---|---|
| 3 | 0.002 |
| 10 | 0.003 |
| 20 | 0.006 |

Alternatively, where lower levels of water are required in the oxidation step, the oxygen-containing gas stream can be passed through a bed of a molecular sieve, such as zeolite 4A, which is effective to remove (e.g., adsorb) water from said stream and produce a dried gas stream containing less than or equal to 0.1% by weight of water. In one embodiment, the molecular sieve can then be treated (e.g., regenerated) to remove at least a portion of the adsorbed water. For example, the molecular sieve may be heated to a temperature sufficient to evaporate at least a portion of adsorbed water. In some embodiments, the molecular sieve may then be reused. However, molecular sieve drying is expensive, and the cost is directly related to the amount of water to be removed. Thus, an optimized process may include both water removal by cooling and/or pressurization followed by passing the gas through a molecular sieve.

The conditions used to effect the oxidation step vary significantly with the type of hydrocarbon substrate to be oxidized, but generally suitable conditions include a temperature of between about 20° C. and about 150° C., such as between about 70° C. and about 130° C. The oxidation step is preferably carried out at a pressure between about 15 kPa and about 500 kPa, such as between 15 kPa to about 150 kPa. The oxidation step can be conducted in a single oxidation reactor or in a series of reactors connected in series. The oxidation reactor may be operated in a batch, semi-batch, or continuous flow manner.

Oxidation Product

The product of the present oxidation process depends on the nature of the hydrocarbon substrate being oxidized but in general is a hydroperoxide, alcohol, ketone, carboxylic acid, or dicarboxylic acid, especially a hydroperoxide.

For example, when the hydrocarbon substrate is isobutane, the oxidation product comprises tertiary butyl hydroperoxide (which is useful as an oxidation reagent and in the production of propylene oxide) and tertiary butanol (which is useful as a gasoline additive).

When the hydrocarbon substrate is cyclohexane, the oxidation product comprises cyclohexyl hydroperoxide, cyclohexanol, and cyclohexanone. Cyclohexyl hydroperoxide is readily decomposed to additional cyclohexanol and cyclohexanone, either thermally or with the assistance of a catalyst. Cyclohexanol can be oxidized with aqueous nitric acid to produce adipic acid, which is a precursor in the synthesis of Nylon 6,6, whereas cyclohexanone can be converted to cyclohexanoxime which undergoes acid-catalyzed rearrangement to produce caprolactam, a precursor in the synthesis of Nylon 6.

Where the hydrocarbon substrate is an alkylaromatic compound of the general formula (II), the product of the oxidation reaction includes a hydroperoxide of general formula (III):

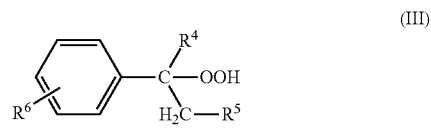

(III)

in which $R^4$, $R^5$ and $R^6$ have the same meaning as in formula (II). Preferably, the hydroperoxide is sec-butylbenzene hydroperoxide or cyclohexylbenzene hydroperoxide. This hydroperoxide can then be converted by acid cleavage to phenol or a substituted phenol and an aldehyde or ketone of the general formula $R^4COCH_2R^5$, in which $R^4$ and $R^5$ have the same meaning as in formula (II). Phenol can of course be reacted with acetone to produce bisphenol A, a precursor in the production of polycarbonates and epoxy resins.

The hydroperoxide cleavage reaction is conveniently effected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 100 $hr^{-1}$, preferably about 1 to about 50 $hr^{-1}$. The hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide, and sulfur trioxide are also effective homogeneous cleavage catalysts. The preferred homogeneous cleavage catalyst is sulfuric acid.

A suitable heterogeneous catalyst for use in the cleavage of sec-butylbenzene hydroperoxide includes a smectite clay, such as an acidic montmorillonite silica-alumina clay, as described in U.S. Pat. No. 4,870,217 (Texaco), the entire disclosure of which is incorporated herein by reference.

The invention will now be more particularly described with reference to the accompanying drawing.

FIG. 1 is a simplified flow diagram of a hydrocarbon oxidation process according to one example of the invention. In this process, the hydrocarbon to be oxidized and an oxidation catalyst, such as N-hydroxyphthalimide, are fed via line 1 to the first of three oxidation reactors 14, 15 and 16 connected in series.

Make-up air, typically at atmospheric pressure, a temperature of 35° C. and containing 3 wt % water, is supplied by line 17 to a steam compressor 18 which, in one embodiment, is operated by 42 bar, absolute (4200 kPa, gauge) steam and produces a compressed air stream via line 19 (e.g., at a temperature of 171° C. and a pressure of 2.5 bar, absolute (250 kPa, gauge)).

The compressed air stream in line 19 is passed through an air/water separator 22, where the condensed liquid water in the air is removed via line 3 to produce a dry compressed air stream, which contains 0.3 wt % or less water in vapor form. The compressed air is then passed via line 23 to each of the three oxidation reactors 14, 15, and 16.

In the first oxidation reactor 14, the hydrocarbon is oxidized by the compressed air to produce a liquid effluent stream, which exits the reactor through line 14 (*a*), and a gaseous spent air stream, which exits the reactor through line 14 (*b*). The liquid effluent stream in line 14 (*a*) is forwarded to the second reactor 15.

In each of the second and third reactors 15 and 16, the partially oxidized effluent stream from reactor 14 is further oxidized by the compressed air to produce a liquid effluent stream, which exits the reactor through line 15 (*a*), 16 (*a*) and then is forwarded to a product recovery section 24. The gaseous spent air stream, which exits the reactor through line 15 (*b*), 16 (*b*) are combined and sent to a gas treatment section 26 before being vented to atmosphere.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Additionally or alternately, the invention can be described by the following embodiments:

1. A process for oxidizing a hydrocarbon to a product comprising at least one of the corresponding hydroperoxide, alcohol, ketone, carboxylic acid and dicarboxylic acid, the process comprising contacting a hydrocarbon with an oxygen-containing compound in at least one oxidation zone in the presence of a catalyst comprising a cyclic imide having an imide group of formula (I):

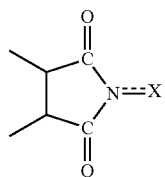

wherein X represents an oxygen atom, a hydroxyl group, or an acyloxy group and wherein the oxygen-containing compound supplied to said at least one oxidation zone has a water content of less than or equal to 0.6% by weight of the oxygen-containing compound.

2. The process of embodiment 1, wherein the oxygen-containing compound is air that has been at least partially dehydrated.

3. The process of embodiment 1, wherein said hydrocarbon comprises an alkane or cycloalkane.

4. The process of embodiment 1, wherein said hydrocarbon comprises isobutane or cyclohexane.

5. The process of embodiment 1, wherein said hydrocarbon comprises cyclohexane, the product comprises cyclohexanol and the process further comprises converting the cyclohexanol to adipic acid.

6. The process of embodiment 1, wherein said hydrocarbon comprises cyclohexane, the product comprises cyclohexanone and the process further comprises converting the cyclohexanone to caprolactam.

7. The process of embodiment 1, wherein said hydrocarbon comprises iso-butane, the product comprises tert-butyl hydroperoxide and the process further comprises using the tert-butyl hydroperoxide as an oxidation catalyst.

8. The process of embodiment 1, wherein said hydrocarbon comprises an alkylaromatic compound of general formula (II):

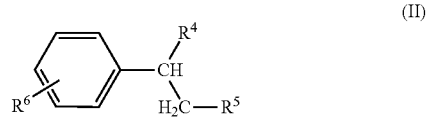

wherein $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group and the product comprises a hydroperoxide of the general formula (III):

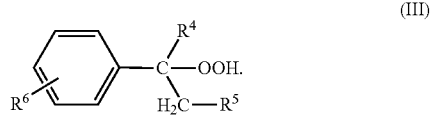

9. The process of embodiment 8, wherein said alkylaromatic compound of general formula (II) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

10. The process of embodiment 8, and further comprising cleaving the hydroperoxide to produce phenol or a substituted phenol.

11. The process of embodiment 1, wherein said cyclic imide is of the general formula (IV):

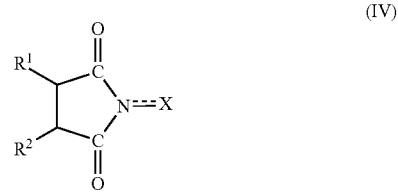

wherein X represents an oxygen atom, a hydroxyl group, or an acyloxy group and $R^1$ and $R^2$ are the same or different and each represents a hydrogen atom, a halogen atom, an alkyl group, an aryl group, a cycloalkyl group, a hydroxyl group, an alkoxy group, a carboxy group, an alkoxycarbonyl group, or an acyl group, provided that $R^1$ and $R^2$ may be bonded together to form a double bond or an aromatic or non-aromatic ring.

12. The process of embodiment 1, wherein said cyclic imide is of the general formula (V):

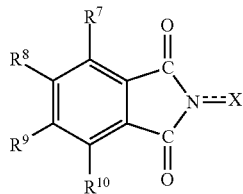

wherein X represents an oxygen atom, a hydroxyl group and each of $R^7$, $R^8$, $R^9$, and $R^{10}$ is independently selected from H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I and/or $NO_2$.

13. The process of embodiment 1, wherein said cyclic imide comprises N-hydroxyphthalimide.

14. The process of embodiment 1, wherein said oxygen-containing compound supplied to said oxidation zone has a water content of less than or equal to 0.3% by weight of the oxygen-containing compound.

15. The process of embodiment 1, wherein said oxygen-containing compound supplied to said oxidation zone has a water content of less than or equal to 0.1% by weight of the oxygen-containing compound.

16. The process of embodiment 1 and further comprising:
(a) cooling an oxygen-containing gas stream to a temperature of less than about 20° C. and/or pressurizing said gas stream to a pressure between about 50 KPa, gauge to about 1000 KPa, gauge;
(b) passing the cooled and/or pressurized gas stream through a gas/liquid separator to reduce the water content of said gas stream to less than or equal to 0.6% by weight of the gas stream; and
(c) supplying said gas stream from (b) to said at least one oxidation zone as the oxygen-containing compound.

17. The process of embodiment 16, wherein the oxygen-containing gas stream is cooled to a temperature of between about 5° C. and about 10° C.

18. The process of embodiment 16, wherein the oxygen-containing gas stream is pressurized to a pressure between about 150 KPa, gauge to about 500 KPa, gauge.

19. The process of embodiment 1 and further comprising:
(d) passing an oxygen-containing gas stream through a bed of a molecular sieve which is effective to adsorb water from said stream and produce a dried gas stream containing less than or equal to 0.1% by weight of water; and
(e) supplying said dried gas stream to said at least one oxidation zone as the oxygen-containing compound.

20. The process of embodiment 19, wherein said molecular sieve is zeolite 4A.

21. The process of embodiment 20, further comprising treating the molecular sieve to remove at least a portion of the adsorbed water.

22. The process of embodiment 21, wherein the treating comprises heating the molecular sieve to a temperature sufficient to evaporate at least a portion of adsorbed water.

23. The process of embodiment 1 and further comprising:
(a) cooling an oxygen-containing gas stream to a temperature of less than about 20° C. and/or pressurizing said gas stream to a pressure between about 50 KPa, gauge to about 1000 KPa, gauge, such as between about 150 KPa, gauge to about 500 KPa, gauge;
(b) passing the cooled and/or pressurized gas stream through a gas/liquid separator to reduce the water content of said gas stream to less than or equal to 0.6% by weight;
(c) passing the gas stream from (b) through a bed of a molecular sieve, such as zeolite 4A, which is effective to remove further water from said stream and produce a dried gas stream containing less than or equal to 0.1% by weight of water; and
(d) supplying said dried gas stream said at least one oxidation zone as the oxygen-containing compound.

24. A process for producing phenol, the process comprising:
(a) hydroalkylating benzene with hydrogen in the presence of a hydroalkylation catalyst under conditions effective to produce a hydroalkylation reaction product comprising cyclohexylbenzene;
(b) separating at least a portion of the cyclohexylbenzene from the hydroalkylation reaction product;
(c) obtaining dehydrated air having a water content of less than or equal to 0.6% by weight;
(d) contacting at least a portion of the cyclohexylbenzene from the separating step (b) with the dehydrated air in the presence of an oxidation catalyst comprising a cyclic imide in an oxidation zone under oxidation conditions effective to produce an oxidation product comprising cyclohexylbenzene hydroperoxide and cyclic imide catalyst; and
(e) contacting at least a portion of the oxidation product comprising cyclohexylbenzene hydroperoxide with a cleavage catalyst under cleavage conditions effective to convert at least part of the cyclohexylbenzene hydroperoxide into phenol and cyclohexanone.

25. The process of embodiment 24, wherein the dehydrated air in step (c) is obtained by:
(i) cooling the air to a temperature of less than about 20° C. and/or pressurizing the air to a pressure between about 50 KPa, gauge to about 1000 KPa, gauge; and
(ii) passing the cooled and/or pressurized gas stream through a gas/liquid separator to reduce the water content of said gas stream to less than or equal to 0.6% by weight.

The invention claimed is:
1. A process for oxidizing a hydrocarbon to a product comprising at least one of the corresponding hydroperoxide, alcohol, ketone, carboxylic acid and dicarboxylic acid, the process comprising contacting a hydrocarbon with air that has been at least partially dehydrated in at least one oxidation zone in the presence of a catalyst comprising a cyclic imide having the general formula (IV):

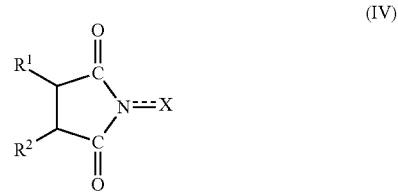

wherein X represents an oxygen atom, a hydroxyl group, or an acyloxy group, and $R^1$ and $R^2$ are the same or different and each represents a hydrogen atom, a halogen atom, an alkyl group, an aryl group, a cycloalkyl group, a hydroxyl group, an alkoxy group, a carboxyl group, an alkoxycarbonyl group, or an acyl group, provided that $R^1$ and $R^2$ may be bonded together to form a double bond or an aromatic- or non-aromatic ring; and further wherein the air supplied to said at least one oxidation zone has a water content of less than or equal to 0.1% by weight of the air.

2. The process of claim 1, wherein said hydrocarbon comprises an alkane or cycloalkane.

3. The process of claim 1, wherein said hydrocarbon comprises isobutane or cyclohexane.

4. The process of claim 1, wherein said hydrocarbon comprises an alkylaromatic compound of general formula (II):

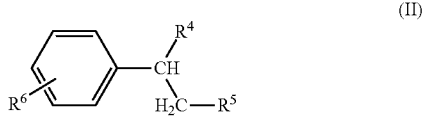

(II)

wherein $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group and the product comprises a hydroperoxide of the general formula (III):

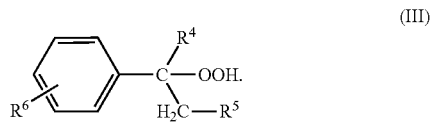

(III)

5. The process of claim 4, wherein said alkylaromatic compound of general formula (II) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

6. The process of claim 4, and further comprising cleaving the hydroperoxide to produce phenol or a substituted phenol.

7. The process of claim 1, wherein said cyclic imide is of the general formula (V):

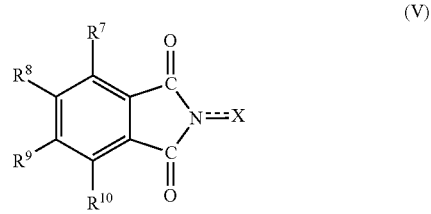

(V)

wherein X represents an oxygen atom, a hydroxyl group and each of $R^7$, $R^8$, $R^9$, and $R^{10}$ is independently selected from H, aliphatic or aromatic alkoxy radical, carboxyl radical, alkoxycarbonyl radical or hydrocarbon radical, each of which has 1 to 20 carbon atoms, $SO_3H$, $NH_2$, OH, F, Cl, Br, I, and/or $NO_2$.

8. The process of claim 1, wherein said cyclic imide comprises N-hydroxyphthalimide.

9. The process of claim 1 wherein said air supplied to said oxidation zone has been dehydrated by a process comprising:
 (a) cooling the air to a temperature of less than about 20° C. and/or pressurizing said air to a pressure between about 50 KPa, gauge to about 1000 KPa, gauge;
 (b) passing the cooled and/or pressurized air through a gas/liquid separator to reduce the water content of said air to less than or equal to 0.6% by weight of the air; and
 (c) supplying said air from (b) to said at least one oxidation zone.

10. The process of claim 9, wherein the air in (a) is cooled to a temperature of between about 5° C. and about 10° C.

11. The process of claim 9, wherein the air in (a) is pressurized to a pressure between about 150 KPa, gauge to about 500 KPa, gauge.

12. The process of claim 1 wherein said air supplied to said oxidation zone has been dehydrated by a process comprising:
 (d) passing the air through a bed of a molecular sieve which is effective to adsorb water from said air such that said air contains less than or equal to 0.1% by weight of water; and
 (e) supplying said air from (d) to said at least one oxidation zone.

13. The process of claim 12, wherein said molecular sieve is zeolite 4A.

14. The process of claim 13, further comprising treating the molecular sieve to remove at least a portion of the adsorbed water.

15. The process of claim 14, wherein the treating comprises heating the molecular sieve to a temperature sufficient to evaporate at least a portion of adsorbed water.

16. The process of claim 1 wherein said air supplied to said oxidation zone has been dehydrated by a process comprising:
 (a) cooling the air to a temperature of less than about 20° C. and/or pressurizing said air to a pressure between about 50 KPa, gauge to about 1000 KPa, gauge, such as between about 150 kPa, gauge to about 500 KPa, gauge;
 (b) passing the cooled and/or pressurized air through a gas/liquid separator to reduce the water content of said air to less than or equal to 0.6% by weight;
 (c) passing the air from (b) through a bed of a molecular sieve which is effective to remove further water from said air from (b), such that said air from (b) contains less than or equal to 0.1% by weight of water; and
 (d) supplying said air from (c) to said at least one oxidation zone.

* * * * *